US009767608B2

(12) United States Patent
Lee et al.

(10) Patent No.: US 9,767,608 B2
(45) Date of Patent: Sep. 19, 2017

(54) AUGMENTED REALITY IMAGE DISPLAY SYSTEM AND SURGICAL ROBOT SYSTEM COMPRISING THE SAME

(71) Applicant: SAMSUNG ELECTRONICS CO., LTD., Suwon-si, Gyeonggi-do (KR)

(72) Inventors: Hee Kuk Lee, Suwon-si (KR); Won Jun Hwang, Seoul (KR); Kyung Shik Roh, Seongnam-si (KR); Jung Yun Choi, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 691 days.

(21) Appl. No.: 14/132,782

(22) Filed: Dec. 18, 2013

(65) Prior Publication Data

US 2014/0275760 A1    Sep. 18, 2014

(30) Foreign Application Priority Data

Mar. 13, 2013    (KR) ........................ 10-2013-0026615

(51) Int. Cl.
*A61B 1/00* (2006.01)
*G06T 19/00* (2011.01)
*A61B 5/00* (2006.01)
*A61B 34/30* (2016.01)
*A61B 34/37* (2016.01)
*A61B 90/92* (2016.01)
*A61B 90/94* (2016.01)
(Continued)

(52) U.S. Cl.
CPC ........ *G06T 19/006* (2013.01); *A61B 1/00045* (2013.01); *A61B 1/00149* (2013.01);
(Continued)

(58) Field of Classification Search
CPC ... A61B 90/36; A61B 1/04; A61B 2034/2055; A61B 2090/376; A61B 34/20;
(Continued)

(56) References Cited

U.S. PATENT DOCUMENTS 7,774,044 B2 *   8/2010   Sauer ..................... G02B 7/002
                                                          345/8
8,398,541 B2 *   3/2013   DiMaio ............. A61B 19/2203
                                                          348/211.3
(Continued)

FOREIGN PATENT DOCUMENTS

JP       2010-200894        9/2010
KR    10-2010-0078034        7/2010
KR    10-2011-0042277        4/2011

*Primary Examiner* — John P Leubecker
*Assistant Examiner* — Arnaldo Torres Diaz
(74) *Attorney, Agent, or Firm* — Harness, Dickey & Pierce, P.L.C.

(57) ABSTRACT

An augmented reality image display system may be implemented together with a surgical robot system. The surgical robot system may include a slave system performing a surgical operation, a master system controlling the surgical operation of the slave system, an imaging system generating a virtual image of the inside of a patient's body, and an augmented reality image display system including a camera capturing a real image having a plurality of markers attached to the patient's body or a human body model. The augmented reality image system may include an augmented reality image generator which detects the plurality of markers in the real image, estimates the position and gaze direction of the camera using the detected markers, and generates an augmented reality image by overlaying a region of the virtual image over the real image, and a display which displays the augmented reality image.

19 Claims, 11 Drawing Sheets

(51) Int. Cl.
*A61B 1/04* (2006.01)
*A61B 5/055* (2006.01)
*A61B 6/03* (2006.01)
*A61B 90/00* (2016.01)
*A61B 34/20* (2016.01)

(52) U.S. Cl.
CPC ............ *A61B 5/7445* (2013.01); *A61B 34/30* (2016.02); *A61B 34/37* (2016.02); *A61B 90/92* (2016.02); *A61B 90/94* (2016.02); *A61B 1/04* (2013.01); *A61B 5/055* (2013.01); *A61B 6/032* (2013.01); *A61B 90/361* (2016.02); *A61B 2034/2065* (2016.02); *A61B 2090/365* (2016.02); *A61B 2090/3937* (2016.02); *G06T 2210/41* (2013.01)

(58) Field of Classification Search
CPC ............ A61B 3/113; A61B 2034/2072; A61B 2090/363; A61B 2090/368; A61B 8/4263; A61B 8/4416; G06F 3/012; G02B 2027/0138
USPC .... 600/101, 103, 117, 166, 424; 345/633, 8, 345/106
See application file for complete search history.

(56) References Cited

U.S. PATENT DOCUMENTS

| | | | | |
|---|---|---|---|---|
| 8,489,235 B2 * | 7/2013 | Moll | .................. | A61B 19/2203 700/1 |
| 8,730,266 B2 * | 5/2014 | Brown | .................. | A61B 3/113 345/633 |
| 9,101,397 B2 * | 8/2015 | Guthart | | |
| 9,138,129 B2 * | 9/2015 | Diolaiti | .............. | A61B 1/00163 |
| 9,232,984 B2 * | 1/2016 | Guthart | .................. | A61B 34/20 |
| 9,289,267 B2 * | 3/2016 | Sauer | .................... | A61B 19/52 |
| 2005/0093889 A1 * | 5/2005 | Sauer | .................... | G06T 19/003 345/633 |
| 2005/0181340 A1 * | 8/2005 | Haluck | ................. | G09B 23/285 434/258 |
| 2005/0203380 A1 * | 9/2005 | Sauer | .................... | G02B 7/002 600/417 |
| 2005/0206583 A1 * | 9/2005 | Lemelson | .......... | A61B 1/00048 345/7 |
| 2006/0281971 A1 * | 12/2006 | Sauer | .................... | A61B 19/52 600/109 |
| 2007/0236514 A1 * | 10/2007 | Agusanto | ........... | A61B 1/00193 345/646 |
| 2010/0274087 A1 * | 10/2010 | Diolaiti | .............. | A61B 1/00087 600/118 |
| 2011/0046483 A1 * | 2/2011 | Fuchs | .................. | A61B 8/4245 600/439 |
| 2011/0254829 A1 | 10/2011 | Agevik et al. | | |
| 2012/0071757 A1 * | 3/2012 | Salcudean | ............ | A61B 8/0841 600/439 |
| 2012/0072873 A1 * | 3/2012 | Park | ........................ | G06F 3/013 715/863 |
| 2013/0218340 A1 * | 8/2013 | Hager | ................... | B25J 9/1671 700/257 |
| 2015/0366628 A1 * | 12/2015 | Ingmanson | ........... | A61B 5/015 600/424 |

\* cited by examiner

FIG. 6
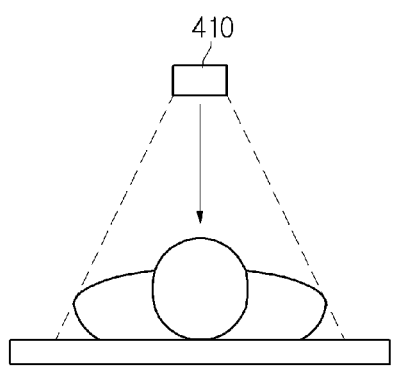 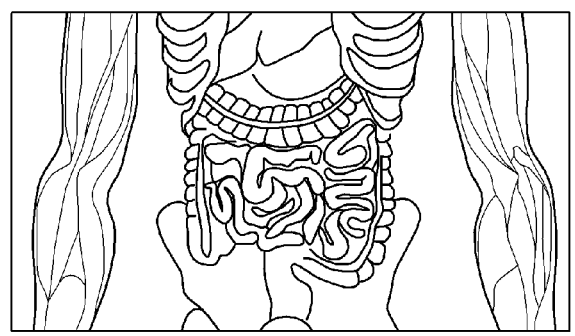

FIG. 8
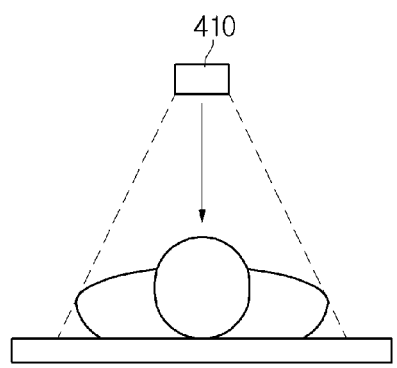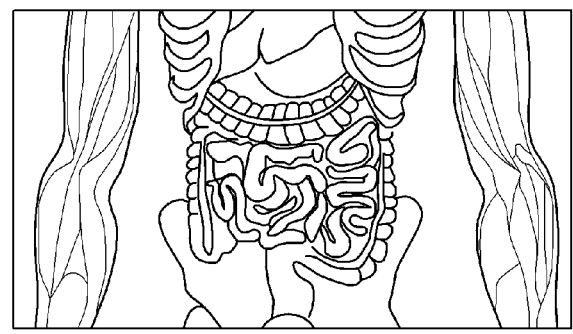

FIG. 9
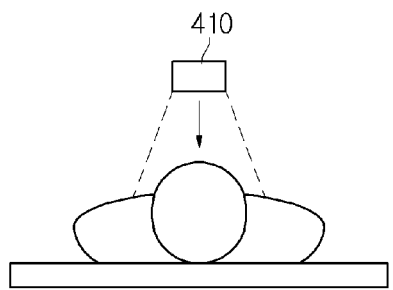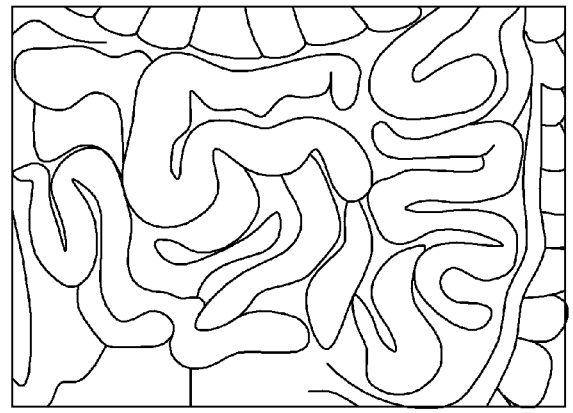

AUGMENTED REALITY IMAGE DISPLAY SYSTEM AND SURGICAL ROBOT SYSTEM COMPRISING THE SAME

CROSS-REFERENCE TO RELATED APPLICATIONS

This application claims the priority benefit of Korean Patent Application No. 10-2013-0026615, filed on Mar. 13, 2013 in the Korean Intellectual Property Office, the disclosure of which is incorporated herein by reference.

BACKGROUND

1. Field

Embodiments disclosed herein relate to an augmented reality image display system to display a virtual image of a region corresponding to movement of a user gaze direction in real-time and a surgical robot system including the same.

2. Description of the Related Art

Minimally invasive surgery generally refers to surgery capable of minimizing incision size and recovery time. Different from laparotomy, which uses relatively large surgical incisions through a part of a human body (e.g., the abdomen), minimally invasive surgery involves much smaller incisions. For example, in minimally invasive surgery, after forming at least one small incision (or invasive hole) of about 0.5 cm to about 1.5 cm through the abdominal wall, an operator inserts an endoscope and surgical tools through the incision to perform surgery while viewing images provided via the endoscope.

As compared with laparotomy, minimally invasive surgery generally causes less post-operative pain, faster recovery of bowel movement, earlier restoration of ability to eat, shorter hospitalization, faster return to daily life, and better cosmetic effects owing to the small incision size. Due to these properties, minimally invasive surgery is used for many different types of surgeries, including cholecystectomy, prostatic carcinoma surgery, hernia repair, and the like, and applications thereof continue to grow.

In general, a surgical robot used in minimally invasive surgery may include a master device and a slave device. The master device may generate a control signal in accordance with manipulation of a doctor and transmit the control signal to the slave device. The slave device may receive the control signal from the master device and performs manipulation required for surgery upon a patient. The master device and the slave device may be integrated with each other, or may be separately arranged in an operating room.

The slave device may include at least one robot arm. A surgical instrument may be mounted on an end of each robot arm, and in turn a surgical tool may be mounted on an end of the surgical instrument.

In minimally invasive surgery using the aforementioned surgical robot, the surgical tool of the slave device and the surgical instrument provided with the surgical tool, are introduced into a patient's body to perform required procedures. In this case, after the surgical tool and the surgical instrument enter the human body, an internal status may be visible from images acquired by an endoscope which is one of the surgical tools. Medical images of the patient, such as a computed tomography (CT) image and a magnetic resonance imaging (MRI) image, may be acquired before surgery may be used as references.

SUMMARY

Therefore, it is an aspect of the present invention to provide an augmented reality image display system capable of instinctively observing the inside of a patient's body and a surgical robot system including the same.

Additional aspects of the invention will be set forth in part in the description which follows and, in part, will be apparent from the description, or may be learned by practice of the invention.

In accordance with an aspect of the present invention, a surgical robot system includes a slave system performing a surgical operation upon a patient (or object), a master system controlling the surgical operation of the slave system, an imaging system generating a virtual image of the inside of the patient's body, and an augmented reality image display system including a camera capturing a real image having a plurality of markers attached to the patient's body or a human body model, an augmented reality image generator detecting the plurality of markers in the real image, estimating position and gaze direction of the camera using the detected markers, and generating an augmented reality image by overlaying a region of the virtual image corresponding to the estimated position and gaze direction of the camera over the real image, and a display displaying the augmented reality image.

The surgical robot system may include a surgical tool to perform a surgical operation, an endoscope to capture an image of a region inside of the patient or object, a position sensor to detect a position of the surgical tool, and a position calculator to calculate position information of the surgical tool using detected signals by the position sensor.

The augmented reality image generator may receive position information of the surgical tool from the slave system and generate a virtual surgical tool at a region matching the position information in the augmented reality image. The augmented reality image may include a virtual image of a surgical tool inserted into the patient or object.

The camera may be attached to the display and the augmented reality image generator may generate the augmented reality image by estimating the position and gaze direction of the camera changing in accordance with movement of the display in real-time and by compositing a region of the virtual image corresponding to the estimated position and gaze direction of the camera and the real image.

The augmented reality image generator may calculate the position information of each of the detected markers in the real image and estimate the position and gaze direction of the camera using the calculated position information of each of the markers. The position information of each of the markers may include a distance between the markers and a connection angle between the markers. The position information of each of the markers may include size information of the marker in the real image.

The augmented reality image generator may calculate a distance between a marker and the camera by calculating a size of the marker and comparing the calculated size with a predefined size of the marker.

The augmented reality image generator may generate the augmented reality image by calculating a distance between the camera and the marker using the size information of the marker, and may enlarge or contract the virtual image in accordance with the calculated distance, and composite the virtual image and the real image.

The imaging system may include a three-dimensional (3D) image conversion unit to convert an image of the patient or object captured in advance of the surgical operation, into a 3D image, a virtual image generator to generate a virtual image by projecting the converted 3D image onto the image acquired by the endoscope, and an image storage unit to store the 3D image and the virtual image.

The image of the patient or object captured in advance of the surgical operation may include at least one of a computed tomography (CT) image and a magnetic resonance imaging (MRI) image.

The augmented reality image may be generated to have a region corresponding to the position and gaze direction of the camera to face forward.

In accordance with another aspect of the present invention, an augmented reality image display system includes a camera capturing a real image having a plurality of markers attached to an object (e.g., a patient's body or a human body model), an augmented reality image generator detecting the plurality of markers in the real image, estimating position and gaze direction of the camera using the detected markers, and generating an augmented reality image by overlaying a region of a virtual image corresponding to the estimated position and gaze direction of the camera over the real image, and a display displaying the augmented reality image.

In accordance with another aspect of the present invention, an augmented reality image display system may include a first camera to capture from a first view a first image of an object and a plurality of markers attached to the object, a communication unit to receive a virtual image generated by projecting a three-dimensional image of the object onto a second image of the object captured by a second camera from a second view, and an augmented reality image generator to generate a composite image by compositing the virtual image over the first image, based upon a distance between the first camera and the object, and a relative direction from which the first camera faces the object.

The first image may correspond to a real image captured from an external view of the object, and the second image may correspond to a real image captured from an internal view of the object by a camera disposed within the object.

The augmented reality image generator may calculate the relative direction and the distance between the first camera and the object by using at least one of a calculated distance between the markers, connection angle between the markers, size of the markers, and pre-defined identification information of each of the markers.

The augmented reality image generator may receive position information of a tool inserted inside of the object and generate a virtual tool at a matching region of the composite image, and the augmented reality image generator may generate the composite image by compositing the virtual image, the first image, and the generated virtual tool.

In accordance with another aspect of the present invention, an augmented reality image display method includes: capturing, by a first camera from a first view, a first image of an object and a plurality of markers attached to the object, receiving a virtual image generated by projecting a three-dimensional image of the object onto a second image of the object captured from a second view, and generating a composite image by compositing the virtual image over the first image, based upon a distance between the first camera and the object, and a relative direction from which the first camera faces the object.

The generating may include calculating the relative direction and the distance between the first camera and the object by using at least one of a calculated distance between the markers, connection angle between the markers, size of the markers, and pre-defined identification information of each of the markers.

The method may further include receiving position information of a tool inserted inside of the object and generating a virtual tool at a matching region of the composite image, and generating the composite image by compositing the virtual image, the first image, and the generated virtual tool.

BRIEF DESCRIPTION OF THE DRAWINGS

These and/or other aspects of the invention will become apparent and more readily appreciated from the following description of the embodiments, taken in conjunction with the accompanying drawings of which:

FIGS. 6 and 7 are augmented reality images in accordance with gaze direction of a camera;

FIGS. 8 and 9 are augmented reality images each composited of a real image and a virtual image contracted or enlarged in proportion to distance between a camera and each marker;

DETAILED DESCRIPTION

Figure 1:
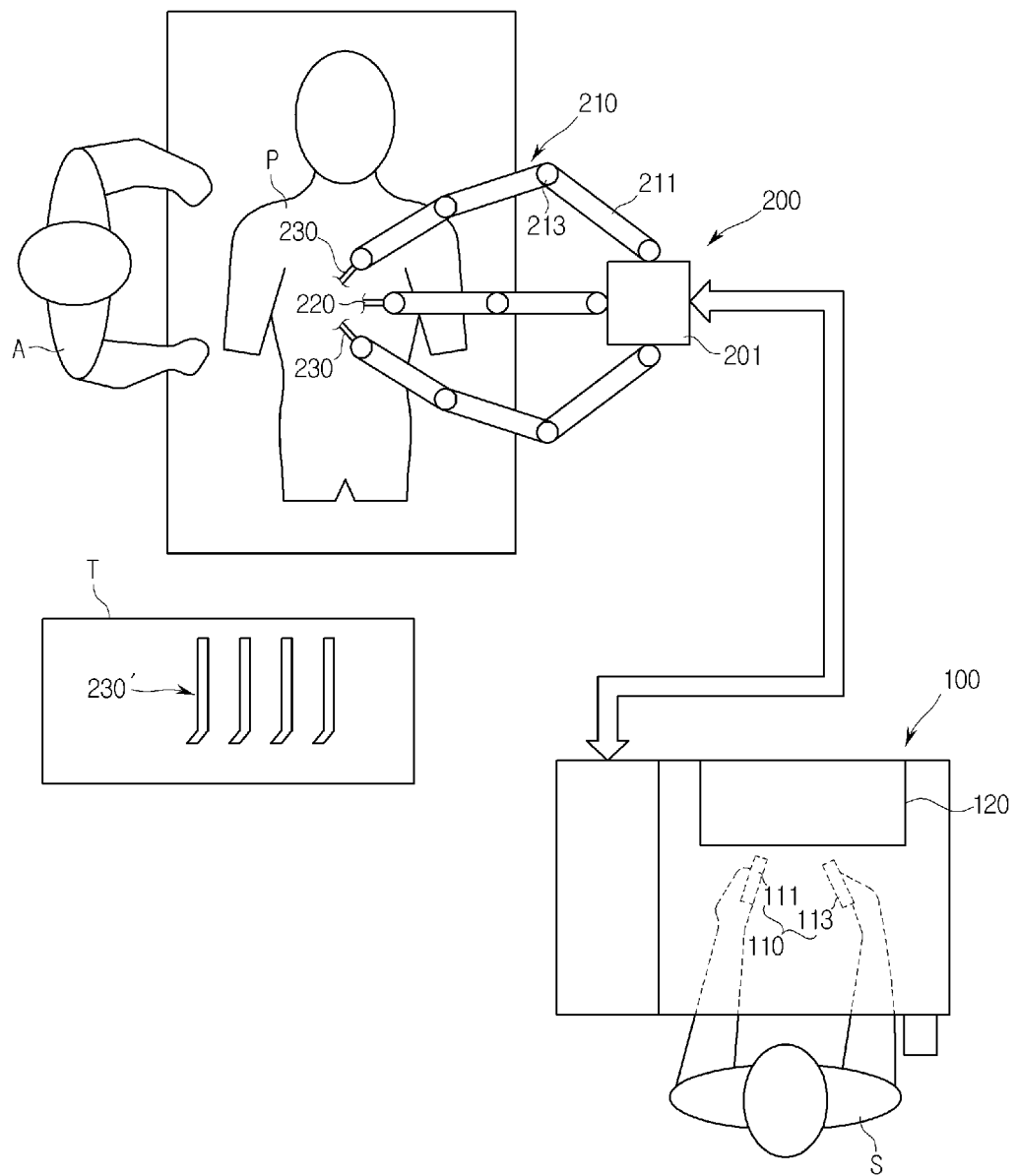
FIG. 1 is a diagram schematically illustrating an outer appearance of a surgical robot system.

The aspects, particular advantages and novel features of the embodiments of the present invention will become apparent with reference to the following detailed description and embodiments described below in detail in conjunction with the accompanying drawings. In the drawings, the same or similar elements are denoted by the same reference numerals even though they are depicted in different drawings. In the following description of the embodiments, a detailed description of known functions and configurations incorporated herein will be omitted when it may make the subject matter of the embodiments rather unclear. Herein, the terms first, second, etc. are used simply to discriminate any one element from other elements, and the elements should not be limited by these terms.

Hereinafter, embodiments of the present invention will be described in detail with reference to the accompanying drawings.

Figure 2:
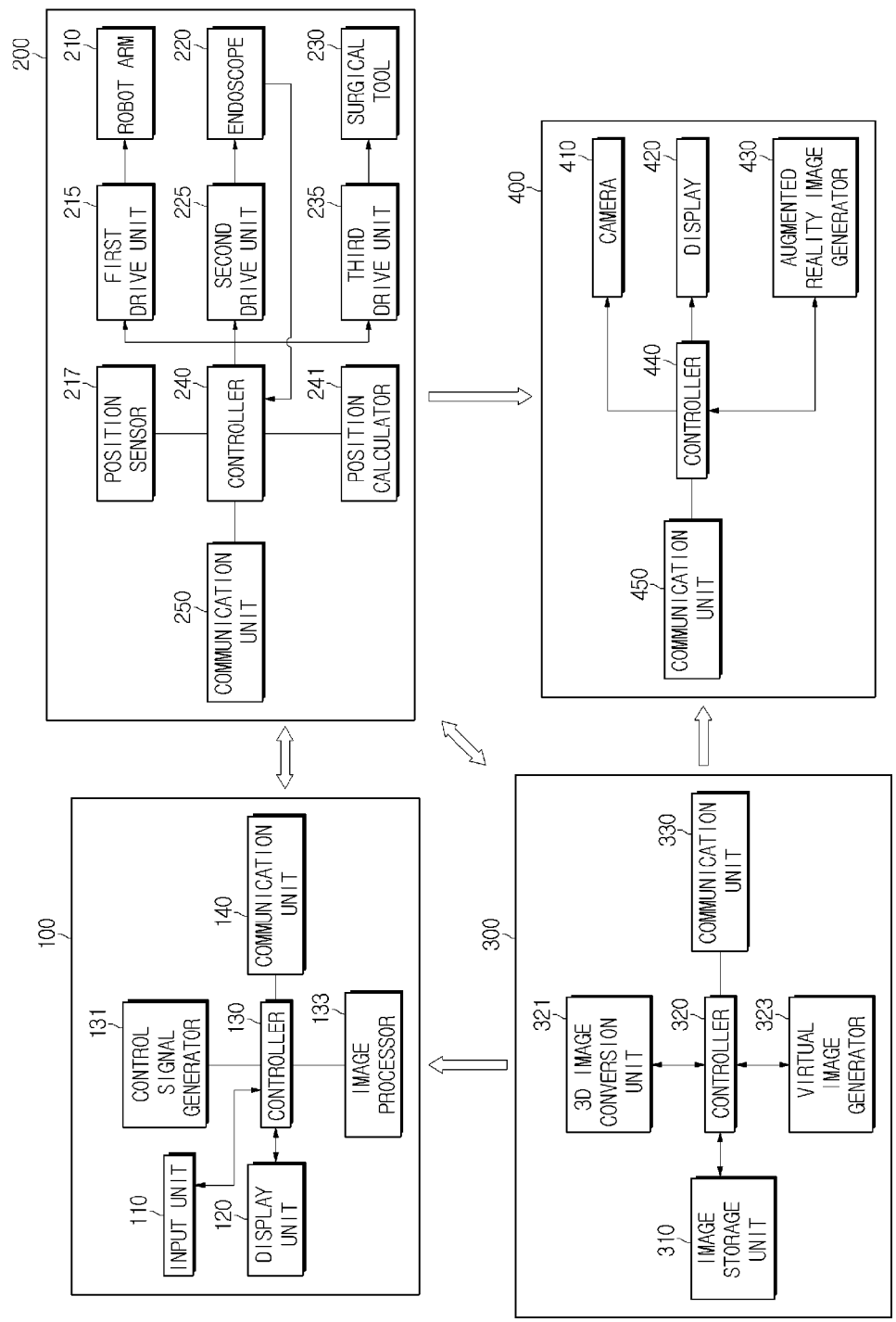
FIG. 2 is a block diagram schematically illustrating constituent elements of a surgical robot system.

FIG. 1 is a diagram schematically illustrating an outer appearance of a surgical robot system. FIG. 2 is a block diagram schematically illustrating constituent elements of a surgical robot system.

A surgical robot system may include a slave system 200 that performs surgery upon a patient P who lies on an operating table, and a master system 100 that remotely controls the slave system 200 in accordance with manipulation of a user or an operator S (e.g., a doctor). In this regard, at least one other (e.g., an assistant A) assisting the operator S may be positioned near the patient P. The slave system 200 and the master system 100 may be connected over a wired or wireless network, or a combination thereof.

In this regard, assisting the operator S may refer to assisting a surgical operation while surgery is in progress. For example, the assistant may perform tasks such as replacing surgical tools, move a robot arm, but such tasks are not limited thereto. For example, a variety of surgical instruments may be used according to the surgical operation to be performed. Since the number of robot arms 210 of the slave system 200 is limited, the number of surgical tools mounted thereon at once is also limited. One or a plurality of surgical tools may be mounted on a robot arm. Accordingly, when the surgical tool needs to be replaced during surgery, the operator S instructs the assistant A positioned near the patient P to replace the surgical tool. In accordance with the instruction, the assistant A removes a surgical tool not in use from the robot arm 210 of the slave system 200 and mounts another surgical tool placed on a tray T on the corresponding robot arm 210. Alternatively, if an assistant is not present or available, the operator may need to leave the master system 100 to replace a surgical tool at the slave system 200.

The master system 100 and the slave system 200 may be separately arranged as physically independent devices, without being limited thereto. For example, the master system 100 and the slave system 200 may be integrated with each other as a single device.

As illustrated in FIGS. 1 and 2, the master system 100 may include an input unit 110 and a display unit 120.

The input unit 110 may refer to an element that receives an instruction for selection of an operation mode of the surgical robot system or an instruction for remote control of the operation of the slave system 200 input by the operator S. For example, the input unit 110 may include a haptic device, a clutch pedal, a switch, and a button, but is not limited thereto. For example, a voice recognition device may be used. The input unit 110 may also include a keys, joystick, keyboard, mouse, touch screen, to enable a user to control the surgical robot. The input unit 110 may include one or a combination of input devices. Hereinafter, a haptic device will be exemplarily described as an example of the input unit 110.

FIG. 1 exemplarily illustrates that the input unit 110 includes two handles 111 and 113, but the present embodiment is not limited thereto. For example, the input unit 110 may also include one handle or three or more handles as well.

The operator S may respectively manipulate two handles 111 and 113 using both hands as illustrated in FIG. 1 to control operation of the robot arm 210 of the slave system 200. Although not shown in detail in FIG. 1, each of the handles 111 and 113 may include an end effector, a plurality of links, and a plurality of joints.

In this regard, the end effector may have a pencil or stick shape with which a hand of the operator S is in direct contact, without being limited thereto.

A joint refers to a connection between two links and may have 1 degree of freedom (DOF) or greater. Here, "degree of freedom (DOF)" refers to a DOF with regard to kinematics or inverse kinematics. A DOF of a mechanism indicates the number of independent motions of a mechanism or the number of variables that determine independent motions at relative positions between links. For example, an object in a 3D space defined by X-, Y-, and Z-axes has at least one DOF selected from the group consisting of 3 DOFs to determine a spatial position of the object (a position on each axis), 3 DOFs to determine a spatial orientation of the object (a position on each axis), and 3 DOFs to determine a spatial orientation of the object (a rotation angle relative to each axis). More specifically, it will be appreciated that when an object is movable along each of X-, Y-, and Z-axes and is rotatable about each of X-, Y-, and Z-axes, it will be appreciated that the object has 6 DOFs.

In addition, a detector (not shown) may be mounted on the joint. The detector may detect information indicating the state of the joint, such as force/torque information applied to the joint, position information of the joint, and speed information when in motion. Accordingly, in accordance with manipulation of the input unit 110 by the operator S, the detector (not shown) may detect information regarding the status of the manipulated input unit 110, and the controller 130 may generate a control signal corresponding to information regarding the status of the input unit 110 detected by the detector (not shown) by use of a control signal generator 131 to transmit the generated control signal to the slave system 200 via a communication unit 140. That is, the controller 130 of the master system 100 may generate a control signal according to manipulation of the input unit 110 by the operator S using the control signal generator 131 and transmit the generated control signal to the slave system 200 via the communication unit 140.

The display unit 120 of the master system 100 may display a real image of the inside of the patient P's body acquired by the endoscope 220 and a 3D image generated using a medical image of the patient P captured before surgery. To this end, the master system 100 may include an image processor 133 that receives image data from the slave system 200 and the imaging system 300 and outputs the image information to the display unit 120. In this regard, "image data" may include a real image of the inside of the patient P's body acquired by the endoscope 220 and a 3D image generated using a medical image of the patient P before surgery as described above, but is not limited thereto.

The display unit 120 may include at least one monitor, and each monitor may be implemented to individually display information required for surgery. For example, when the display unit 120 includes three monitors, one of the monitors may display the real image of the inside of the patient P's body acquired by the endoscope 220 or the 3D image generated using a medical image of the patient P before surgery, and the other two monitors may respectively display information regarding the status of motion of the slave system 200 and information regarding the patient P. In this regard, the number of monitors may vary according to the type and kind of information to be displayed. The display unit 120 may be embodied by, for example, a Liquid Crystal Display (LCD), light emitting diode (LED) display, organic light emitting diode (OLED) display, plasma display panel (PDP), cathode ray tube (CRT), and the like.

Here, "information regarding the patient" may refer to information indicating vital signs of the patient, for example, bio-information such as body temperature, pulse, respiration, and blood pressure. In order to provide such bio-information to the master system 100, the slave system 200, which will be described later, may further include a bio-information measurement unit including a body temperature-measuring module, a pulse-measuring module, a respiration-measuring module, a blood pressure-measuring module, and the like. To this end, the master system 100 may further include a signal processor (not shown) to receive bio-information from the slave system 200, process the bio-information, and output the processed information on the display unit 120. In addition, information (for example, bio-information such as body temperature, pulse, respiration, and blood pressure) regarding the operator or user of the master system 100 may be collected or obtained. Information regarding the operator or user of the master system 100 may be obtained via a sensor, for example, which may be disposed in the input unit 110, for example.

The slave system 200 may include a plurality of robot arms 210 and various surgical tools 230 may be mounted on ends of the robot arms 210. The robot arms 210 may be coupled to a body 201 in a fixed state and supported thereby as illustrated in FIG. 1. In this regard, the numbers of the surgical tools 230 and the robot arms 210 used at once may vary according to various factors, such as diagnostic methods, surgical methods, and spatial limitations of the operating room.

In addition, each of the robot arms 210 may include a plurality of links 211 and a plurality of joints 213. Each of the joints 213 may connect links 211 and may have 1 DOF or greater.

In addition, a first drive unit 215 to control motion of the robot arm 210 according to the control signal received from the master system 100 may be mounted on each of the joints of the robot arm 210. For example, when the operator S manipulates the input unit 110 of the master system 100, the master system 100 generates a control signal corresponding to the status information of the manipulated input unit 110 and transmits the control signal to the slave system 200, and a controller 240 of the slave system 200 drives the first drive unit 215 in accordance with the control signal received from the master system 100, so as to control motion of each joint of the robot arm 210. Here, a substantial control process such as rotation and movement of the robot arm 210 in accordance with manipulation of the input unit 110 by the operator S would be understood by one of ordinary skill in the art, and thus a detailed description thereof will not be given.

Meanwhile, each joint of the robot arm 210 of the slave system 200 may move according to the control signal received from the master system 100 as described above. However, the joint may also be moved by external force. That is, a user (for example the assistant A or operator S) may be positioned near the operating table and may manually move each of the joints of the robot arm 210 to control the location of the robot arm 210, or the like.

Although not illustrated in FIG. 1, the surgical tool 230 may include a housing mounted on an end of the robot arm 210 and a shaft extending from the housing by a predetermined length.

A drive wheel may be coupled to the housing. The drive wheel may be connected to the surgical tool 230 via a wire, or the like, and the surgical tool 230 may be driven via rotation of the drive wheel. To this end, a third drive unit 235 may be mounted on one end of the robot arm 210 for rotation of the drive wheel. For example, in accordance with manipulation of the input unit 110 of the master system 100 by the operator S, the master system 100 generates a control signal corresponding to information regarding the status of the manipulated input unit 110 and transmits the generated control signal to the slave system 200, and the controller 240 of the slave system 200 drives the third drive unit 235 according to the control signal received from the master system 100, so as to drive the surgical tool 230 in a desired manner. However, the operating mechanism of the surgical tools 230 is not necessarily constructed as described above, and various other electrical/mechanical mechanisms to realize required motions of the surgical tool 230 may also be employed.

Examples of the surgical tool 230 may include a skin holder, a suction line, a scalpel, scissors, a grasper, a surgical needle, a needle holder, a stapler, a cutting blade, and the like, without being limited thereto. Other examples of surgical tools may include micro-dissector, tacker, suction irrigation tool, clip applier, irrigator, catheter, suction orifice, surgical knife, surgical forceps, a cautery (i.e., a tool for burning or cutting a diseased part by using electric energy or heat energy), and the like. Any known tools required for surgery may also be used. That is, surgical tool 230 may refer to any tool or device which may be used to perform an operation such as surgery.

In general, the surgical tools 230 may be classified into main surgical tools and auxiliary surgical tools. Here, "main surgical tools" may refer to surgical tools performing direct surgical motion, such as cutting, suturing, cauterization, and rinsing, on the surgical region, for example, a scalpel or surgical needle. "Auxiliary surgical tools" may refer to surgical tools that do not perform direct motion in the surgical region and assist motion of the main surgical tools, for example, a skin holder.

Likewise, the endoscope 220 does not perform direct motions on a surgical region and is used to assist a motion of the main surgical tool. Thus, the endoscope 220 may be considered an auxiliary surgical tool in a broad sense. The endoscope 220 may include various surgical endoscopes, such as a thoracoscope, an arthroscope, a rhinoscope, a cysotoscope, a rectoscope, a duodenoscope, and a cardioscope, in addition to a laparoscope that is generally used in robotic surgery.

In addition, the endoscope 220 may include a complementary metal-oxide semiconductor (CMOS) camera and a charge coupled device (CCD), but is not limited thereto. In addition, the endoscope 220 may include a lighting unit to radiate light to the surgical region. The endoscope 220 may also be mounted on one end of the robot arm 210 as illustrated in FIG. 1, and the slave system 200 may further include a second drive unit 225 to drive the endoscope 220. The controller 240 of the slave system 200 may transmit images acquired by the endoscope 220 to the master system 100 and the imaging system 300 via a communication unit 250.

In addition, the slave system 200 according to the illustrated embodiment may include a position sensor 217 to detect a current position of the surgical tool 230 as described above. In this regard, the position sensor 217 may be a potentiometer, an encoder, or the like, but is not limited thereto.

The position sensor 217 may be mounted on each joint of the robot arm 210 provided with the surgical tool 230. The position sensor 217 detects information regarding the status of motion of each joint of the robot arm 210. The controller 240 receives the detected information from the position sensor 217 and calculates the current position of the surgical tool 230 using a position calculator 241. The position calculator may calculate the current position of the surgical tool 230 by applying the input information to kinematics of the robot arm 210. In this regard, the calculated current position may be coordinate values. In addition, the controller 240 may transmit the calculated coordinate values of the position of the surgical tool 230 to an augmented reality image display system 400, which will be described later.

As described above, since the current position of the surgical tool 230 is estimated by detecting the status of each joint of the robot arm 210 provided with the surgical tool 230, the position of the surgical tool 230 may be efficiently estimated even when the surgical tool 230 is located outside the field of vision of the endoscope 220, or when the field of vision of the endoscope 220 is blocked by internal organs, or the like.

In addition, although not illustrated in FIG. 1, the slave system 200 may further include a display unit (not shown) that may display an image of a surgical region of the patient P acquired by the endoscope 220. The display unit may be embodied by, for example, a Liquid Crystal Display (LCD), light emitting diode (LED) display, organic light emitting diode (OLED) display, plasma display panel (PDP), cathode ray tube (CRT), and the like.

The imaging system 300 may include an image storage unit 310 to store a 3D image generated using a medical image of the patient P before surgery, a virtual image obtained by projecting the 3D image onto an image acquired by the endoscope 220, and the like. In this regard, "medical image before surgery" may include a computed tomography (CT) image, a magnetic resonance imaging (MRI) image, a positron emission tomography (PET) image, a single photon emission computed tomography (SPECT) image, an ultrasonography (US) image, or the like, without being limited thereto.

To this end, the imaging system 300 may include a 3D image conversion unit 321 to convert the medical image of the patient P before surgery into a 3D image and a virtual image generator 323 to generate a virtual image by projecting the 3D image onto a real image acquired by the endoscope 220 and received from the slave system 200.

Particularly, a controller 320 of the imaging system 300 may receive a medical image from a medical image database DB constructed with medical images of patients captured before surgery, such as CT images or MRI images, convert the received medical image into a 3D image via the 3D image conversion unit 321, and store the obtained 3D image in the image storage unit 310. In addition, the controller 320 may receive a real image of the surgical region of the patient P acquired by the endoscope 220 and received from the slave system 200. For example, an image acquired by the endoscope may be stored in the image storage unit 310. The controller 320 may generate a virtual image obtained by projecting the 3D image onto the received real image by the virtual image generator 323, and store the generated virtual image in the image storage unit 310. As described above, the 3D image and the virtual image stored in the image storage unit 310 may be transmitted to the master system 100, the slave system 200, and the augmented reality image display system 400, which will be described later, through a communication unit 330. The image storage unit 310 may include a storage medium, such as a nonvolatile memory device, such as a Read Only Memory (ROM), Programmable Read Only Memory (PROM), Erasable Programmable Read Only Memory (EPROM), and flash memory, a volatile memory device such as a Random Access Memory (RAM), a hard disc, and an optical disc, or combinations thereof. However, examples of the storage unit are not limited to the above description, and the storage unit may be realized by other various devices and structures as would be understood by those skilled in the art.

The imaging system 300 may be integrated with the master system 100 or the slave system 200, without being limited thereto, and may also be separated therefrom as an independent device.

According to the illustrated embodiment, the augmented reality image display system 400 may include a camera 410 that captures a real image including a plurality of markers attached to the patient's body or a human body model, an augmented reality image generator 430 that detects the plurality of markers in the real image acquired by the camera 410, estimates position and gaze direction of the camera 410 using the detected markers, and generates an augmented reality image by overlaying a virtual image of a corresponding region over the real image, and a display 420 that displays the augmented reality image, as illustrated in FIG. 2. The augmented reality image display system 400 may further include a controller 440 which controls the operations of the camera 410, display 420, augmented reality image generator 430, and communication unit 450. The communication unit 450 may be used to transmit and receive information to the master system 100, the slave system 200, and the imaging system 300. Communication may be performed among the master system 100, the slave system 200, the imaging system 300, and the augmented reality image display system 400 via a wired or wireless network, or a combination thereof.

In the illustrated embodiment, the augmented reality image display system 400 may be a head mounted display (HMD), but is not limited thereto. For example, the augmented reality image display system 400 according to the present embodiment may be an eyeglass-type head mounted display (HMD) as illustrated in FIG. 3.

Figure 3:
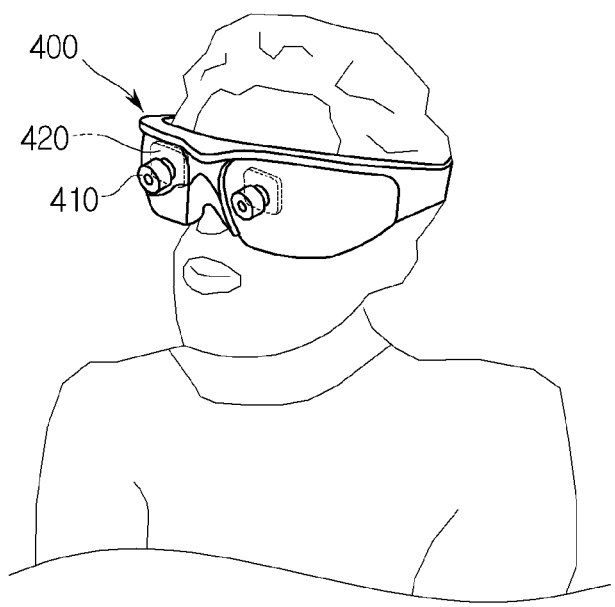
FIG. 3 is a view illustrating an assistant wearing an augmented reality image display system.

The camera 410 that captures real images may be attached to the front surface, i.e., a surface that does not face user's eyes but faces forward, of the augmented reality image display system 400 as illustrated in FIG. 3. That is, the camera 410 is attached to capture images of the forward view from the user. In this regard, the camera 410 may be attached to be parallel to user's eyes as illustrated in FIG. 3, without being limited thereto. By attaching the camera 410 to be parallel to the user's eyes, real images corresponding to the gaze direction of the user may be efficiently acquired. However, this is an exemplary embodiment, and the camera 410 may be attached to any position suitable for capturing images of the forward view from the user. That is, the camera is disposed such that it captures images in a general or same direction that the user views using his or her eyes. For example, for an augmented reality image display system having an inner surface (i.e., a first side facing toward the user's eyes), and an outer surface (i.e., a second side opposite of the first side facing away from the user's eyes), the camera may be disposed on the outer surface. The camera (or cameras) may be positioned on the outer surface to correspond to a position of the user's eyes and capture images in a field of view substantially similar to a field of view of the user.

In addition, the camera 410 may be a complementary metal-oxide semiconductor (CMOS) camera and a charge coupled device (CCD), but is not limited thereto.

Particularly, in the illustrated embodiment, the camera 410 may capture images of the patient P who lies on an operating table or a human body model P'. Alternatively, the camera 410 may capture images of an object for which an operation is being performed on. The human body model P' may be used to facilitate observation of both the front and rear sides of the patient P since the patient P lying on the operating table cannot move during surgery, and thus only one of the front or rear sides of the patient P may be observed.

Figure 4:
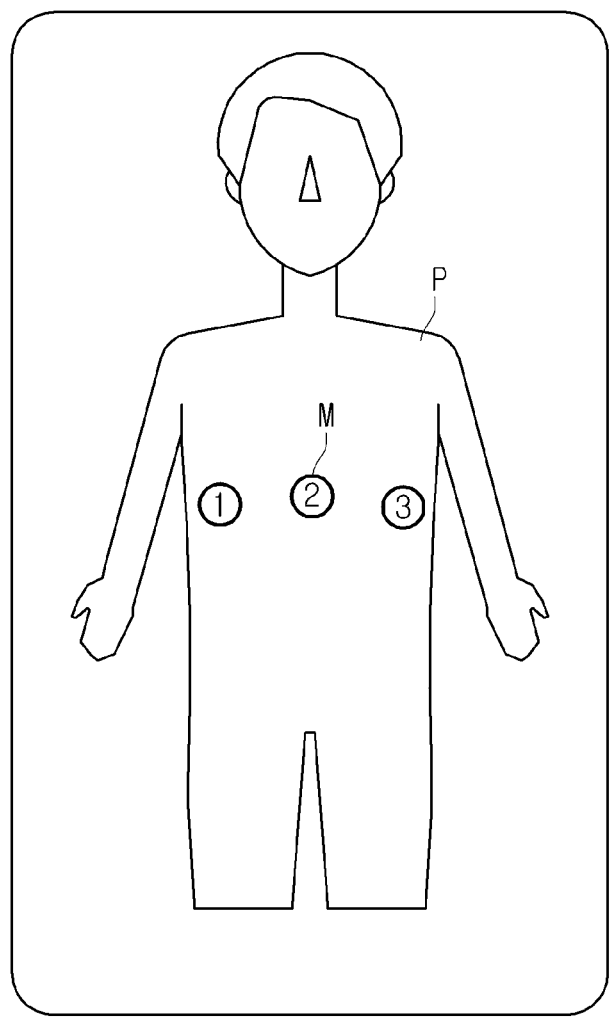
FIG. 4 is a view illustrating a patient's body to which markers are attached.
Figure 5:
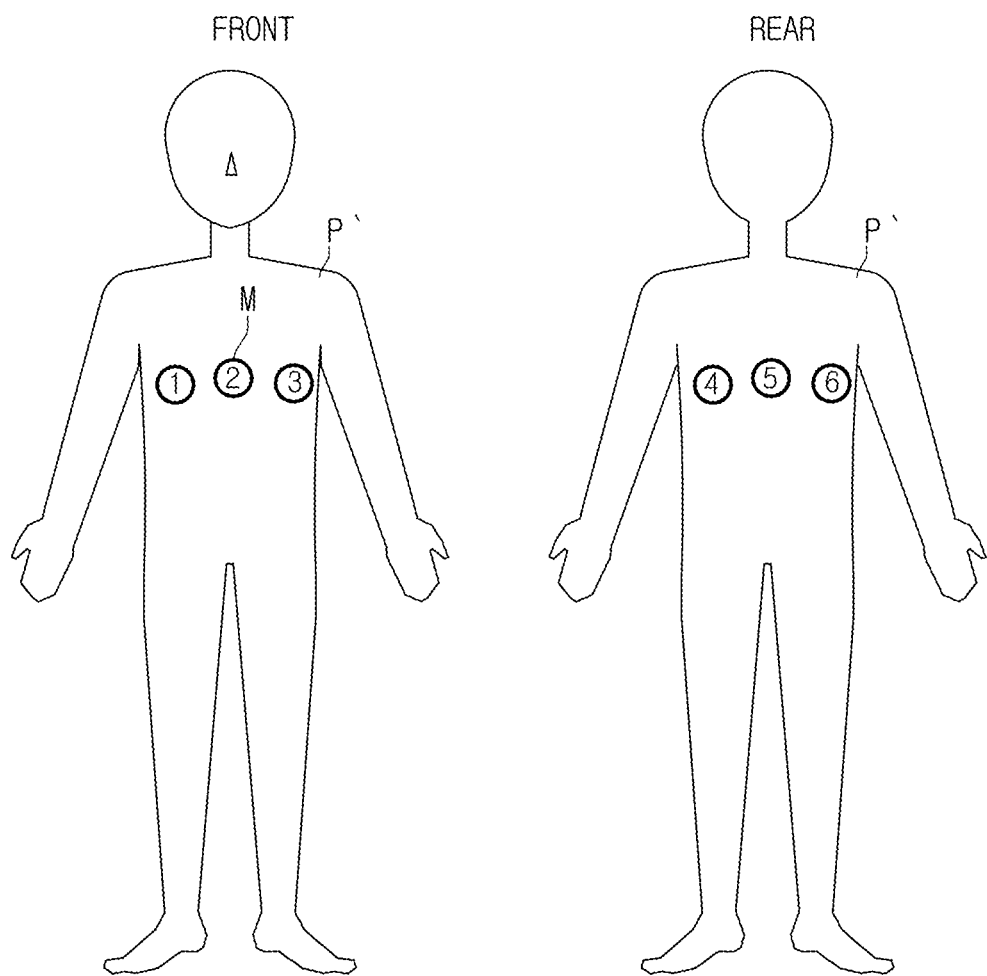
FIG. 5 is a view illustrating a human body model to which markers are attached.

A plurality of markers M may be attached to the surface of the patient P lying on the operating table as illustrated in FIG. 4. Here, "marker M" may refer to an indicator for estimation of the position and gaze direction of the camera 410. In this regard, the markers M may be attached to regions adjacent to the surgical region, without being limited thereto. In addition, although three markers M are exemplarily illustrated in FIG. 4, more markers M may also be attached thereto. In addition, although FIG. 4 exemplarily illustrates three markers M attached in a row for convenience of explanation, the alignment of the attached markers M is not limited thereto, and the markers M may be attached thereto in a triangular or quadrangular form. Alternatively, the markers M may be arranged in the shape of a polygon, a circle, or other geometric shapes, in a non-linear or linear fashion. The markers M may be arranged randomly, or in a predetermined patter. In addition, the markers M may be attached to the surface of the human body model P' as illustrated in FIG. 5. Here, the markers M may be attached to both of the front and rear surfaces of the human body model P'. The markers M may be arranged differently on the rear surface than the front surface, or may have a similar arrangement to correspond to the positioning of the markers M on the front surface.

The markers M illustrated in FIGS. 4 and 5 may have different identification information. In this regard, "identification information" may include information regarding the position to which each marker M is attached, original size of each marker M, and the like, but is not limited thereto. Referring to FIG. 4, marker ① may indicate a position on the right side of the abdomen of the patient, marker ② may indicate a position at the center of the abdomen of the patient, and marker ③ may indicate a position on the left side of the abdomen of the patient. Similarly, marker ④, marker ⑤, and marker ⑥ of FIG. 5 may respectively indicate a position on the left side of the back of the patient, a position at the center of the back of the patient, and a position on the right side of the back of the patient. In addition, the original size of each marker M may be defined in advance.

In addition, FIGS. 4 and 5 exemplarily illustrate the markers distinguished from each other using numbers. The markers may be distinguished from each other using different patterns, different colors, different letters, symbols, and/ or codes, and the like.

Accordingly, a real image acquired by the camera 410 may include a plurality of distinguishable markers having different identification information. The augmented reality image generator 430, which will be described later, may detect the markers contained in the real image, calculate position information of each marker in the real image, and estimate the current position and gaze direction of the camera 410 using the calculated position information of each marker and the pre-defined identification information of each marker. In this regard, "position information of each marker" may include a distance between markers, a connection angle between markers, size of each marker, and the like, but is not limited thereto.

The augmented reality image generator 430 may generate an augmented reality image by detecting the plurality of markers contained in the real image acquired by the camera 410, calculating position information of each of the detected markers in the real image, estimating the current position and gaze direction of the camera 410 using the calculated position information of each marker and the pre-defined identification information of each marker, and compositing a virtual image of a portion corresponding to the estimated current position and gaze direction of the camera 410 and the real image captured by the camera 410 using an overlay method as described above.

Here, a "virtual image" may include a 3D image generated using a medical image of the patient P before surgery and an image obtained by projecting the 3D image onto an image acquired by the endoscope 220, as described above. That is, a "virtual image" may be an image of the inside of the patient P's body.

In addition, a "real image" may refer to an image of the real world captured by the camera 410 and may be an image of the patient P lying on the operating table or the human body model P' in the illustrated embodiment. The real image may include the markers attached to the patient P or the human body model P'.

The augmented reality image may refer to an image composited by overlaying a virtual image showing the inside of the patient P's body, over the patient P or human body model P' contained in the real image captured by the camera 410, as described above. For example, as illustrated in FIG. 6, a virtual image showing the inside of the patient P's body corresponding to the gaze direction of the camera 410 is overlaid on the patient's body P contained in the real image captured by the camera 410. In this regard, the markers contained in the real image may be removed from the augmented reality image to prevent the user from being confused.

In this regard, the camera 410 may capture an image of a region viewed by the user in real-time, and the augmented reality image generator 430 may receive the real image captured by the camera 410 in real-time so as to generate an augmented reality image in accordance with movement of the camera 410.

Particularly, the augmented reality image generator 430 may receive the real image captured by the camera 410 in real-time, detect the plurality of markers in the received real image, calculate the distance between the markers, connection angle between the markers, and size of each of the markers, and estimate the current position and gaze direction of the camera 410 using the calculated distance between the markers, connection angle between the markers, size of the markers, and pre-defined identification information of each of the markers. In this regard, details of calculating the distance between the markers, the connection angle between the markers, the size of the markers and estimating the current position and gaze direction of the camera 410 would be understood by one of ordinary skill in the art, and thus a detailed description thereof will not be given.

That is, the augmented reality image generator 430 may estimate position and gaze direction of the moving camera 410 in real-time and generate an augmented reality image corresponding to the estimated position and gaze direction of the camera 410 in real-time.

Figure 7:

For example, referring to FIGS. 6 and 7, when the camera 410 faces the abdomen of the patient P at the center of the patient P in a state of being spaced apart from the patient P, the augmented reality image generator 430 receives a real image captured by the camera 410, detects a plurality of markers, estimates that the camera 410 faces the abdomen of the patient P at the center of the patient P in a state of being spaced apart from the patient P using position information of each marker in the real image, and overlays a virtual image of the corresponding region received from the imaging system 300 over the real image. As a result, an augmented reality image in which the center of the abdomen of the patient P faces forward is generated.

In addition, as illustrated in FIG. 7, when the camera 410 diagonally faces the left side of the abdomen of the patient at a position deviated from the center of the abdomen of the patient P in a state of being spaced apart from the patient P, the augmented reality image generator 430 receives a real image captured by the camera 410, detects the markers, estimates that the camera 410 faces the abdomen of the patient P at the left side of the patient P in a state of being spaced apart from the patient P using position information of each marker in the real image, and overlays a virtual image of the corresponding region received from the imaging system 300 over the real image. As a result, an augmented reality image in which the left side of the abdomen of the patient P faces forward is produced.

In this regard, FIGS. 6 and 7 only illustrate that the camera 410 is positioned at the center and the left side of the abdomen of the patient P. However, it is apparent that, while the camera 410 continuously moves, the corresponding augmented reality image may also be output and displayed on the display 420. That is, the augmented reality image generator 430 may generate the augmented reality image tracking the gaze of the user and display the augmented reality image on the display 420. For example, the augmented reality image may be displayed to a user wearing the head mounted display as illustrated in FIG. 3. Alternatively, or additionally, the augmented reality image may be transmitted to the master system 100 and displayed via display unit 120 of the master system 100.

In addition, the augmented reality image generator 430 may calculate a distance between the camera 410 and the marker by calculating the size of the marker detected in the real image captured by the camera 410 and by comparing the calculated size of the marker with a pre-defined size of the marker. That is, the camera 410 calculates a distance from a subject to be shot. In general, as the camera 410 moves away from the subject, the size of the subject decreases. On the other hand, as the camera 410 moves toward the subject, the size of the subject increases. That is, according to the distance between the camera 410 and the subject, the size of the subject increases or decreases in the real image.

Figure 10:
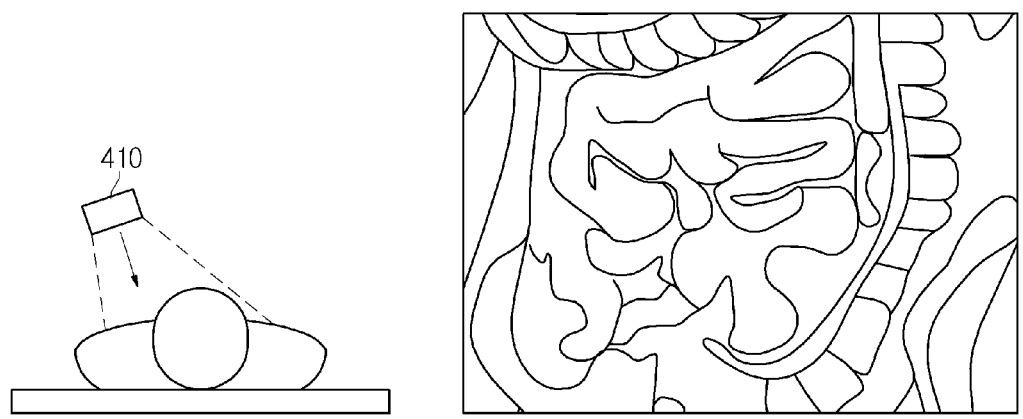
FIG. 10 is an augmented reality image obtained by moving a camera of FIG. 9 while maintaining a distance between the camera and the marker.

Accordingly, the augmented reality image generator 430 may generate the augmented reality image by calculating the distance between the camera 410 and the marker, enlarging or contracting a virtual image of the corresponding region received from the imaging system 300 in accordance with the calculated distance, and compositing the virtual image and the real image. That is, as the distance between the camera 410 and the patient P decreases, the virtual image of the corresponding region is enlarged and then composited with the real image. On the other hand, as the distance between the camera 410 and the patient P increases, the virtual image of the corresponding region is contracted and then composited with the real image. Augmented reality images contracted or enlarged in accordance with the distances between the camera 410 and the patient P are illustrated in FIGS. 8 and 9. In addition, FIG. 10 is an augmented reality image in which the left side of the abdomen of the patient P faces forward when the camera 410 is disposed close to the patient at a position on the left side of the patient P, as compared to FIG. 7, when the camera 410 is disposed relatively further away from the patient at a position on the left side of the patient P.

As described above, the augmented reality image display system 400 according to the illustrated embodiment may observe the corresponding portion of the inside of the patient's body according to the gaze direction of the user in real-time. That is, the augmented reality image may be generated and displayed such that a portion viewed by the user faces forward in real-time in direct response to the gaze direction change of the user. Accordingly, the inside of the patient P's body may be more efficiently observed than by designating the gaze direction and position using an input unit such as a mouse, a keyboard, and a joystick or as compared with a conventional method of observing the inside of the patient P's body.

In addition, the augmented reality image generator 430 may receive current position information of the surgical tool from the slave system 200 to generate a virtual surgical tool at a matching region of the augmented reality image. Here, "position information" may be coordinate values as described above. The augmented reality image generator 430 may generate the virtual surgical tool at coordinates matching the received coordinate values of the surgical tool on the augmented reality image. In this regard, as illustrated in FIG. 11, when the image of the surgical tool is captured by the endoscope 220, the real image of the surgical tool may be displayed at a portion overlapping the virtual surgical tool using the real image of the surgical tool.

Figure 11:
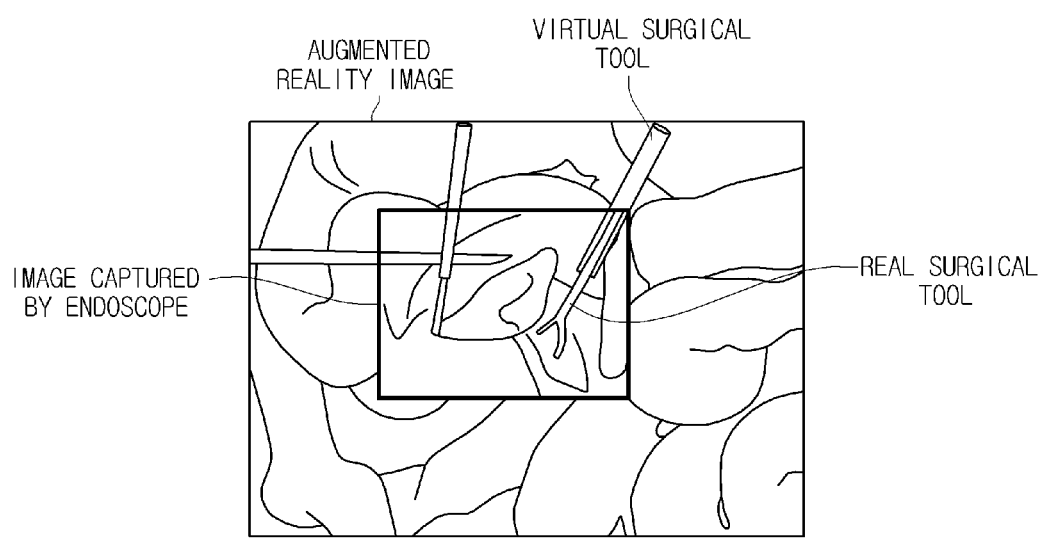
FIG. 11 is an image composited of an image of a surgical region acquired by an endoscope and an augmented reality image having a real image of a surgical tool and a virtual image of the surgical tool.

That is, according to the present embodiment as illustrated in FIG. 11, the augmented reality image may be an image generated by compositing a 3D image generated using the medical image of the patient before surgery, the virtual surgical tool generated using the image acquired by the endoscope 220, and position information of the surgical tool received from the slave system 200. In this regard, when the image acquired by the endoscope 220 does not contain the surgical tool, the augmented reality image may include only the virtual surgical tool. When the real image acquired by the endoscope 220 contains the surgical tool, the virtual surgical tool and the real image of the surgical tool may be composited as illustrated in FIG. 11.

The display 420 may refer to an element to display the augmented reality image generated by the augmented reality image generator 430. The display 420 may be disposed on the rear surface, i.e., a surface facing the user's eyes, of the augmented reality image display system 400, as illustrated in FIG. 3. Here, the display 420 may be a liquid crystal display (LCD), without being limited thereto. For example, the display 420 also may be embodied by, for example, a light emitting diode (LED) display, organic light emitting diode (OLED) display, plasma display panel (PDP), cathode ray tube (CRT), and the like.

According to an embodiment, the assistant A who may directly observe the patient P may use the augmented reality image display system 400. That is, the augmented reality image display system 400 that is a system to instinctively observe the inside of the patient P's body may be used by a user who may directly observe the patient P.

For example, conventionally the assistant A may observe the inside of the patient P's body using a separate monitor in an operating room. In this regard, since the monitor is generally located at a region not adjacent to the patient P, it is impossible for the assistant A to simultaneously observe the patient and watch the monitor. During surgery, in accordance with an instruction to retool the robot arm 210 from the operator S, the assistant A needs to retract the robot arm 210, replace the surgical tool currently used in a state of being inserted into the patient P with another surgical tool, and insert the replaced surgical tool into the patient P. In this case, the surgical tool is located near the patient P and the inside of the patient P's body needs to be checked through the separate monitor. Thus, the assistant A needs to retract the robot arm 210 from the patient P and retool the robot arm 210 while observing the inside of the patient P's body through the monitor. Accordingly, retooling of the surgical tool may be delayed, and peripheral organs and tissues may be damaged during retooling of the surgical tool while observation is not instinctively performed.

However, according to embodiments disclosed herein, when the assistant A assists the surgical operation while wearing the augmented reality image display system 400, the inside of the patient P's body may be instinctively observed through the display 420 that displays the status of the inside of the patient P's body while observing the patient P without watching a separate monitor. Thus, assistant tasks such as retooling of the robot arm 210 may be more quickly and more safely performed. In addition, the assistant A may provide detailed information by observing regions that are missed by the operator S positioned far away from the operating room, thereby improving surgery quality. Furthermore, the augmented reality image may be transmitted to the operator S who may supervise or observe the tasks performed by the assistant A.

Meanwhile, in an embodiment, laparoscopic surgery is an example of a surgical system performed directly by the operator S upon the patient using a surgical tool inserted into the patient P without using a surgical robot system remotely controlled by the operator S. When the operator S directly performs surgery while wearing the augmented reality image display system 400 according to the present embodiment during laparoscopic surgery, the real image of the region of the patient's body viewed by the operator S is displayed, and thus the surgical region covered by skin may be more efficiently observed. As a result, damage of organs and tissues which may be caused during surgery may be prevented.

While the disclosure herein has provided example embodiments of a surgical robot and control method to control the surgical robot, for example, in a medical setting to perform an operation on a patient (e.g., a human or animal or other life form), the disclosure is not so limited. For example, the disclosure may be directed to a robot used in other settings which may benefit from the surgical robot and augmented reality image display system disclosed herein. For example, the robot and augmented reality image display system may be utilized to perform operations in any confined space or enclosure in which an operator may need to perform controlled movements using an instrument attached to a robot arm, so as to avoid or to prevent injuries to bodies or objects, that may be located or disposed within the space or enclosure, due to imprecise movements of the robot. The settings may include, for example, mining operations, surveillance operations, inspection operations, repair operations, bomb disposal operations, etc., however again, the disclosure is not so limited. Further, while the operator may be a doctor, the operator generally may be any user who uses the surgical robot or robot as disclosed herein, and need not be a doctor.

The apparatus and methods for controlling a configuration or operation mode of the surgical robot and augmented reality image display system according to the above-described example embodiments may use one or more processors. For example, a processing device may be implemented using one or more general-purpose or special purpose computers, such as, for example, a processor, an image processor, a controller and an arithmetic logic unit, a central processing unit (CPU), a graphics processing unit (GPU), a digital signal processor (DSP), a microcomputer, a field programmable array, a programmable logic unit, an application-specific integrated circuit (ASIC), a microprocessor or any other device capable of responding to and executing instructions in a defined manner.

The terms "module", and "unit," as used herein, may refer to, but are not limited to, a software or hardware component or device, such as a Field Programmable Gate Array (FPGA) or Application Specific Integrated Circuit (ASIC), which performs certain tasks. A module or unit may be configured to reside on an addressable storage medium and configured to execute on one or more processors. Thus, a module or unit may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules/units may be combined into fewer components and modules/units or further separated into additional components and modules.

Some example embodiments of the present disclosure can also be embodied as a computer readable medium including computer readable code/instruction to control at least one component of the above-described example embodiments. The medium may be any medium that can storage and/or transmission the computer readable code.

Aspects of the above-described example embodiments may be recorded in non-transitory computer-readable media including program instructions to implement various operations embodied by a computer. The media may also include, alone or in combination with the program instructions, data files, data structures, and the like. The program instructions recorded on the media may be those specially designed and constructed for the purposes of the example embodiments, or they may be of the kind well-known and available to those having skill in the computer software arts. Examples of non-transitory computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. The media may be transfer media such as optical lines, metal lines, or waveguides including a carrier wave for transmitting a signal designating the program command and the data construction. Examples of program instructions include both machine code, such as produced by a compiler, and files containing higher level code that may be executed by the computer using an interpreter. The described hardware devices may be configured to act as one or more software modules in order to perform the operations of the above-described example embodiments, or vice versa. In addition, a non-transitory computer-readable storage medium may be distributed among computer systems connected through a network and computer-readable codes or program instructions may be stored and executed in a decentralized manner. In addition, the computer-readable storage media may also be embodied in at least one application specific integrated circuit (ASIC) or Field Programmable Gate Array (FPGA). Some or all of the operations performed by the surgical robot according to the above-described example embodiments may be performed over a wired or wireless network, or a combination thereof.

Each block of the flowchart illustrations may represent a unit, module, segment, or portion of code, which comprises one or more executable instructions for implementing the specified logical function(s). It should also be noted that in some alternative implementations, the functions noted in the blocks may occur out of the order. For example, two blocks shown in succession may in fact be executed substantially concurrently or the blocks may sometimes be executed in the reverse order, depending upon the functionality involved. Also, while an illustration may show an example of the direction of flow of information for a process, the direction of flow of information may also be performed in the opposite direction for a same process or for a different process.

Although a few example embodiments of the present invention have been shown and described, it would be appreciated by those skilled in the art that changes may be made to these embodiments without departing from the principles and spirit of the invention, the scope of which is defined in the claims and their equivalents.

What is claimed is:

1. A surgical robot system, comprising:
    a slave system including a controller configured to perform a surgical operation upon an object, the slave system including an endoscope configured to capture an interior image of a region inside of the object that includes at least a portion of a surgical tool;
    a master system including a controller configured to control the surgical operation of the slave system by providing control signals to the slave system; and
    an imaging system including a controller configured to generate a virtual image of an inside of the object; and
    an augmented reality image display system including a camera, a display and a controller configured to,
        control the camera to capture a real image of the object and a plurality of markers attached to the object,
        detect a plurality of markers in the real image,
        estimate a position and gaze direction of the camera using the detected markers,
        generate an augmented reality image by overlaying a region of the virtual image corresponding to the estimated position and gaze direction of the camera over the real image, generating a virtual tool corresponding to the surgical tool, and combining the virtual tool and the interior image of the surgical tool captured by the endoscope with the virtual image such that the surgical tool and the virtual tool overlap within the augmented reality image, and
        control the display to display the augmented reality image.

2. The surgical robot system according to claim 1, wherein the slave system comprises:
    the surgical tool, the surgical tool being a tool for performing the surgical operation;
    a position sensor to detect a position of the surgical tool; and
    a position calculator to calculate position information of the surgical tool using detected signals by the position sensor.

3. The surgical robot system according to claim 2, wherein the controller of the augmented reality image display system is configured to receive position information of the surgical tool from the slave system and generate the virtual tool at a region matching the position information in the augmented reality image.

4. The surgical robot system according to claim 1, wherein:
    the camera is attached to the display; and
    the controller of the augmented reality display system is configured to generate the augmented reality image by estimating the position and gaze direction of the camera changing in accordance with movement of the display in real-time and by compositing a region of the virtual image corresponding to the estimated position and gaze direction of the camera and the real image.

5. The surgical robot system according to claim 1, wherein the controller of the augmented reality display system is configured to calculate position information of each of the detected markers in the real image and estimate the position and gaze direction of the camera using the calculated position information of each of the markers.

6. The surgical robot system according to claim 5, wherein the position information of each of the markers includes a distance between the markers and a connection angle between the markers.

7. The surgical robot system according to claim 5, wherein the position information of each of the markers includes size information of a first marker from among the plurality of markers in the real image.

8. The surgical robot system according to claim 7, wherein the controller of the augmented reality image display system is configured to generate the augmented reality image by calculating a distance between the camera and the first marker using the size information of the first marker, enlarge or contracts the virtual image in accordance with the calculated distance, and composite the virtual image and the real image.

9. The surgical robot system according to claim 1, wherein the controller of the imaging system is configured to,
    convert an image of the object captured in advance of the surgical operation, into a 3-D image;
    generate the virtual image by projecting the converted 3-D image onto the interior image captured by the endoscope; and
    store the 3-D image and the virtual image.

10. The surgical robot system according to claim 9, wherein the image of the object captured in advance of the surgical operation includes at least one of a computed tomography (CT) image and a magnetic resonance imaging (MRI) image.

11. The surgical robot system according to claim 1, wherein the augmented reality image is generated to have a region corresponding to the position and gaze direction of the camera to face forward.

12. An augmented reality image display system comprising:
    a camera configured to capture a real image of an object and a plurality of markers attached to the object;
    a controller configured to,
        detect a plurality of markers in the real image,
        estimate a position and gaze direction of the camera using the detected markers, and
        generate an augmented reality image by overlaying a region of a virtual image corresponding to the estimated position and gaze direction of the camera over the real image, generating a virtual tool corresponding to a surgical tool, and combining the virtual tool and an image of the surgical tool with the virtual image such that the surgical tool and the virtual tool overlap within the augmented reality image, the image of the surgical tool being an image captured inside the object by an endoscope; and
    a display configured to display the augmented reality image.

13. The augmented reality image display system according to claim 12, wherein:
    the camera is attached to the display; and
    the controller of the augmented reality image display system is configured to generate the augmented reality image by estimating the position and gaze direction of the camera changing in accordance with movement of the display in real-time and by compositing a region of the virtual image corresponding to the estimated position and gaze direction of the camera and the real image.

14. The augmented reality image display system according to claim 12, wherein the controller of the augmented reality image display system is configured to calculate position information of each of the detected markers in the real image and estimate a position and gaze direction of the camera using the calculated position information of each of the markers.

15. The augmented reality image display system according to claim 14, wherein the position information of each of the markers includes a distance between the markers and a connection angle between the markers.

16. The augmented reality image display system according to claim 14, wherein the position information of each of the markers includes size information of a first marker from among the markers in the real image.

17. The augmented reality image display system according to claim 16, wherein the controller of the augmented reality image display system is configured to,
    generate the augmented reality image by calculating a distance between the camera and the first marker using the size information of the first marker,
    enlarge or contract the virtual image in accordance with the calculated distance, and
    composite the virtual image and the real image.

18. The augmented reality image display system according to claim 12, wherein the augmented reality image includes the virtual image of the surgical tool inserted into the object.

19. The augmented reality image display system according to claim 12, wherein the augmented reality image is generated to have a region corresponding to the position and gaze direction of the camera to face forward.

\* \* \* \* \*